United States Patent
Pauser et al.

(10) Patent No.: US 10,016,257 B2
(45) Date of Patent: Jul. 10, 2018

(54) PEN-LIKE DISPENSER FOR A DENTAL MATERIAL

(71) Applicant: 3M INNOVATIVE PROPERTIES COMPANY, St. Paul, MN (US)

(72) Inventors: Helmut Pauser, Diessen (DE); Marc Peuker, Schöndorf (DE); Mathias Bertl, Wildsteig (DE); Bruce R. Broyles, Oakdale, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 14/785,029

(22) PCT Filed: Apr. 28, 2014

(86) PCT No.: PCT/US2014/035687
§ 371 (c)(1),
(2) Date: Oct. 16, 2015

(87) PCT Pub. No.: WO2014/179219
PCT Pub. Date: Nov. 6, 2014

(65) Prior Publication Data
US 2016/0074136 A1    Mar. 17, 2016

(30) Foreign Application Priority Data
Apr. 30, 2013  (EP) .................................... 13165944

(51) Int. Cl.
*A61C 5/04* (2006.01)
*A61C 5/06* (2006.01)
(Continued)

(52) U.S. Cl.
CPC ............ *A61C 5/062* (2013.01); *A61C 1/0061* (2013.01); *A61C 5/50* (2017.02); *A61C 5/62* (2017.02)

(58) Field of Classification Search
CPC ......... A61C 5/062; A61C 5/04; A61C 1/0061; A61C 5/40; A61C 5/60; A61C 5/62; A61C 5/64; A61C 5/50; A61C 17/02
(Continued)

(56) References Cited

U.S. PATENT DOCUMENTS 3,339,810 A  *  9/1967  Block ................. B65D 83/0011
                                                    222/387
4,949,875 A  *  8/1990  Kuo .................... A46B 11/0006
                                                    222/156
(Continued)

FOREIGN PATENT DOCUMENTS

DE    20 2006 009 628 U1    6/2006
DE       202006 009628      6/2007
(Continued)

OTHER PUBLICATIONS

International search report for PCT International Application# PCT/US2014/035687 dated Sep. 3, 2014, 6 pages.*
(Continued)

*Primary Examiner* — Heidi M Eide (57) ABSTRACT

A pen-like dispenser for dispensing a dental material has a handle and a cover which are attached for rotation relative to each other about a longitudinal axis of the dispenser, and a cartridge for holding the dental material and a screw plunger for extruding the dental material from the cartridge by screwing action. The cartridge and the cover in combination form a rotary slide valve which is operable by rotation about the longitudinal axis between a storage position, in which the cover closes a dispensing outlet of the cartridge, and a dispensing position, in which an opening in the cover opens the dispensing outlet of the cartridge. A relative rotation between the screw plunger and the handle about the longitudinal axis is restricted, and a relative rotation
(Continued)

between the cartridge and the cover about the longitudinal axis is enabled within a predetermined rotation angle and restricted otherwise.

14 Claims, 6 Drawing Sheets

(51) Int. Cl.
  *A61C 1/00* (2006.01)
  *A61C 5/50* (2017.01)
  *A61C 5/62* (2017.01)
(58) Field of Classification Search
  USPC .............................. 433/90, 80, 89
  See application file for complete search history.

(56) References Cited

U.S. PATENT DOCUMENTS

| | | | | |
|---|---|---|---|---|
| 5,364,267 | A * | 11/1994 | Fischer | A61C 19/10 |
| | | | | 206/369 |
| D419,236 | S * | 1/2000 | Carlson | D24/112 |
| 7,128,246 | B2 * | 10/2006 | Raia | B05C 17/00579 |
| | | | | 222/327 |
| 8,834,158 | B2 * | 9/2014 | Leiner | A61C 5/062 |
| | | | | 222/390 |
| 2002/0076671 | A1 * | 6/2002 | Evers | A61C 5/66 |
| | | | | 433/90 |
| 2004/0065689 | A1 * | 4/2004 | Pritchett | B05B 11/3011 |
| | | | | 222/321.7 |
| 2006/0223027 | A1 * | 10/2006 | Smith | A61C 5/62 |
| | | | | 433/90 |
| 2012/0064481 | A1 * | 3/2012 | Cannon | B65D 83/0011 |
| | | | | 433/90 |
| 2012/0272996 | A1 * | 11/2012 | Jimenez | A46B 11/0024 |
| | | | | 132/308 |
| 2012/0322028 | A1 * | 12/2012 | Cheetham | A61C 9/0026 |
| | | | | 433/90 |
| 2013/0032241 | A1 * | 2/2013 | Yamaguchi | A61C 5/062 |
| | | | | 141/2 |
| 2013/0134188 | A1 * | 5/2013 | Terakawa | B05C 17/00576 |
| | | | | 222/386 |

FOREIGN PATENT DOCUMENTS

| | | | | |
|---|---|---|---|---|
| DE | 202006009628 | U1 * | 10/2007 | ............... A61C 5/62 |
| WO | WO 2002-55406 | | 7/2002 | |
| WO | WO 02055406 | A2 * | 7/2002 | ......... B65D 83/0011 |
| WO | WO 2006-108085 | | 10/2006 | |
| WO | WO 2006108085 | A2 * | 10/2006 | ............... A61C 5/62 |
| WO | WO 2013-016642 | | 1/2013 | |
| WO | WO 2013016642 | A2 * | 1/2013 | ........... A61C 9/0026 |

OTHER PUBLICATIONS

Incoming Written Opinion of the ISA. PCT/US2014/035687. International filing date Apr. 28, 2014.*
International Search report for PCT International Application No. PCT/US2014/035687 dated Sep. 3, 2014, 6 pages.

* cited by examiner

PEN-LIKE DISPENSER FOR A DENTAL MATERIAL

FIELD OF THE INVENTION

The invention relates to a dispenser for a dental material, and in particular a dispenser having a cartridge and a screw plunger for dispensing the dental material from the cartridge.

BACKGROUND ART

Dental composite filling materials often are composites containing a predominant amount of fillers, for example quartz, and a relatively small amount of a flowable monomer. Such composites typically further contain a photo initiator allowing the monomer to be polymerized through light energy. Therefore the dental composite filling material may be applied in a cavity in a patient's tooth and light-cured after application in the patient's tooth.

Typically such dental composite filling materials exhibit a relatively high viscosity and therefore typically require high forces for dispensing from a dispensing device. A dispensing device for dispensing dental composite filling materials is for example disclosed in U.S. Pat. No. 7,128,246 B2. Such a device stores a portion of a dental composite filling material which can be extruded by displacing a piston within the device. The device can be coupled to a hand-held dispensing gun providing a relatively high force for displacing the piston via a hand operable leverage. An alternative dispensing device for dental composite filling materials is disclosed in U.S. Design Pat. Des. 419,236.

WO 2006/108085 A2 discloses a syringe delivery system for dispensing a highly viscous material through a syringe delivery opening. The system includes a syringe barrel having a delivery opening, a plunger including a threaded shaft that threadably engages the syringe barrel for selectively dispensing a viscous material through the delivery opening, and a plunger gripping member in gripping communication with the plunger that includes means for sealing the threaded shaft of the plunger so as to prevent contamination by foreign matter. The syringe has a sheath that covers the threaded shaft of the plunger so as to hide the plunger beneath the sheath. The sheath provides a sealed environment for the threaded shaft so as to prevent entrance or contamination by foreign matter.

Although a variety of dispensers for dental composite filling materials are available there is still a need for a dispenser which is easy to use, which accounts for hygiene requirements in dentistry and which helps maximizing shelf life of the dental material stored therein.

SUMMARY OF THE INVENTION

The invention relates to a dispenser for dispensing a dental material, and in particular to a pen-like dispenser for dispensing a dental material. The dispenser comprises a handle and a cover. The handle and the cover are rotatable relative to each other about a longitudinal axis of the dispenser. The cover has an opening. The dispenser further comprises a cartridge for holding the dental material. The cartridge has a dispensing outlet for the dental material. The dispenser further comprises a screw plunger for extruding the dental material from the cartridge by screwing action. In this regard the term screwing action refers to screwing the screw plunger into the cartridge.

The cartridge and the cover in combination form a rotary slide valve. The rotary slide valve is operable by rotation (of the cover and the handle relative to each other) about the longitudinal axis between a storage position and a dispensing position. In the storage position the cover closes the dispensing outlet of the cartridge, whereas in the dispensing position the opening in the cover opens the dispensing outlet of the cartridge. In the storage position the opening in the cover and the dispensing outlet thus are preferably offset and do not overlap with each other. At least the cover at the opening may comprise a sharp cutting edge delimiting at least a portion of the cover opening. The cutting edge is preferably arranged such that during rotation of the rotary slide valve from the dispensing position toward the storage position the cutting edge penetrates through dental material extruded from the cartridge and protruding from the dispensing outlet. The cutting edge may have a wedge shaped profile extending over a part of or entirely over the circumference of the cover opening with the wedge tapering off toward the cover opening. In one example the cutting edge is formed by a chamfer tapering off toward the opening and having a chamfer angle (included angle between the two wall faces forming the cutting edge) of about 5 degrees to about 30 degrees. In another example the cutting edge is formed by a wall having a wall thickness of about 0.05 mm to 2 mm, preferably 0.05 mm to 0.5 mm and most preferably 0.05 mm to 0.2 mm.

The cartridge may comprise an outlet seal for sealing any gap between the cartridge and the cover in a circumference of the cartridge outlet. In the storage position the outlet seal helps encapsulating the dental material within the cartridge, whereas in the dispensing position the outlet seal hinders dental material in flowing between the cartridge and the cover. The outlet seal may be formed by a sealing lip adjacent the cartridge outlet, by a sealing lip arranged on the cover, or by any other appropriate seal including a separate sealing ring, for example.

The dispenser is adapted such that a relative rotation between the screw plunger and the handle about the longitudinal axis is restricted or blocked. The dispenser is further adapted such that a relative rotation between the cartridge and the cover about the longitudinal axis is enabled within a predetermined rotation angle and restricted or blocked otherwise.

The dispenser is advantageous in that it allows for dispensation of dental material (particularly a dental composite filling material) in the form of a pre-dosed portion. Thus the use of a separate instrument for separating (for example cutting or scraping off) a portion of dental composite filling material from the dispenser is not required. Further the dispenser preferably allows for dispensation of the dental material at a precisely controlled manner and particularly may exhibit minimized afterflow (or run on) of dental composite filling material after suspending dispensation. Although a separate instrument may be used for picking up the pre-dosed portion, any intense interaction (like cutting, abrading, scraping) between the instrument and the dispenser can be minimized. This further helps avoiding bringing any particles abraded or cut from the dispenser into the dental composite filling material due to an interaction between the dispenser and the dental instrument. Further the dispenser is advantageous because it helps providing for a convenient handling, precise dosage and hygienic storage of the dental material.

The rotary slide valve is preferably operable from the storage position to the dispensing position by rotation of the cartridge and the cover relative to each other in a first direction about the longitudinal axis. The rotary slide valve is further preferably operable from the dispensing position to the storage position by rotation of the cartridge and the cover relative to each other in a second direction, opposite of the first direction, about the longitudinal axis.

For the purpose of the present specification, the term "direction in context of a rotation of two parts (for example "first direction" and "second direction") refers to a direction these two parts are rotated relative to each other. The person skilled in the art will understand that the same direction of relative rotation between two parts is for example achieved by holding the first part in place and rotating the second part clockwise, or by rotating the first part counterclockwise and holding the second part in place, or by rotating the first part counterclockwise and rotating the second part clockwise.

Further the dispenser is preferably adapted such that in the dispensing position a relative rotation of the handle and the cover in the first direction about the longitudinal axis causes dental material to be extruded by rotation of the screw plunger and the cartridge relative to each other. This is because in the dispensing position the cover and the cartridge are blocked against further rotation relative to each other in the first direction, and the handle and the screw plunger are generally blocked against rotation relative each other. Accordingly in the dispensing position the relative rotation of the handle and the cover in the first direction about the longitudinal axis also results in a relative rotation of the screw plunger and the cartridge in the first direction about the longitudinal axis.

The dispenser is preferably further adapted such that in the storage position (or starting from the storage position) a relative rotation of the handle and the cover in the first direction about the longitudinal axis causes positioning of the rotary slide valve into the dispensing position. This is because in the storage position the cartridge and the cover are preferably rotatable relative to each other in the first direction about the longitudinal axis. This is irrespective of the fact that in the storage position the cartridge and the cover are blocked against a further rotation relative to each other in the second direction about the longitudinal axis.

The dispenser is preferably further adapted such that in the dispensing position (or starting from the dispensing position) a relative rotation of the handle and the cover in the second direction causes positioning of the rotary slide valve into the storage position. This is because in the dispensing position the cartridge and the cover are preferably rotatable relative to each other in the second direction about the longitudinal axis. This is irrespective of the fact that in the dispensing position the cartridge and the cover are blocked against a further rotation relative to each other in the first direction about the longitudinal axis.

In one embodiment the handle and the cover are mated and in combination form a housing. The opening in the cover preferably forms the only opening into the interior of the housing. Although in the area in which the cover and the handle are mated the cover and the handle each may have open ends such open ends do not form any openings of the housing because these open ends are closed by the mating of the cover and the handle.

The handle and the cover each may be generally cup-shaped. In particular each of the handle and the cover may have a tubular sidewall extending along the longitudinal axis. One end of the sidewall is preferably closed by an end wall and the opposite other end of the sidewall is preferably open. The handle and the cover are preferably mated at their open ends. With respect to the handle it is further referred herein to as "handle sidewall", and "handle end wall". With respect to the cover it is further referred to herein as "cover sidewall" and "cover end wall".

The handle sidewall preferably forms an inner handle wall surface which extends along the longitudinal axis at a non-uniform inner cross-section. Thus in one embodiment the handle inwardly at least over a part of its length extends at a substantially uniform non-circular inner cross-section. In this regard the length of the handle refers to a dimension parallel to the longitudinal axis of the dispenser. Further the handle may be formed of one piece, for example the handle sidewall and the handle end wall may be formed in one piece or monolithically.

The screw plunger preferably comprises an outer cross-section which is shaped to engage with the inner cross-section of the handle. For example the screw plunger may have a threaded portion, and with respect to the threaded portion a mushroomed portion forming the outer cross-section for engagement with the inner cross-section of the handle. Therefore the dispenser is adapted such that a relative rotation between the screw plunger and the handle about the longitudinal axis is restricted but a movement along the longitudinal axis is enabled. Accordingly the handle and the screw plunger are preferably blocked or substantially blocked against rotation relative to each other in the first and second direction about the longitudinal axis. However the handle and the screw plunger are preferably axially displaceable relative to each other along the longitudinal axis.

In a further embodiment the dispenser comprises a return spring for resiliently biasing the cover and the cartridge toward the storage position. Thus the dispenser is preferably adapted to return or reset the cover and the cartridge automatically from the dispensing position to the storage position by spring force. The return spring may be configured such that it provides a force sufficient to return the cover and the cartridge and in addition to thereby cut off dental material extending through the dispensing outlet and cover opening by spring force. Thus the dispenser may be adapted to automatically cut off an extruded portion of the dental material. The return spring may be monolithically formed with either the cartridge or the cover, or may be provided as separate piece.

In a further embodiment a gap is provided between the cartridge and the cover over at least a portion of the cartridge circumference about the longitudinal axis. Thus air present in the gap may interact with the dental material by permeation through a cartridge wall. Monomers present in the dental material may accordingly be hindered in so-called anaerobic polymerization. The cartridge may be generally cup-shaped. In particular the cartridge may have a tubular sidewall extending along the longitudinal axis. One end of the cartridge sidewall is preferably closed by an end wall and the opposite other end of the cartridge sidewall is preferably open. The cartridge may at the open end (appending the tubular sidewall) have a widened section (for example an annular flange) in which a threaded nut may be received. The widened section is preferably widened in diameter (or cross-sectional area) relative to the tubular section. In particular the inner diameter (or inner cross-sectional area) of the widened section is preferably greater than the inner diameter (or inner cross-sectional area) of the tubular section. The threaded nut preferably has a thread for engaging with the thread of the screw plunger. The threaded nut may further be axially and rotationaly fixed or attached within the widened section of the cartridge, for example by a thread connection, by a weld or adhesive connection, or any other appropriate connection.

The ratio between the inner cross-sectional area of the tubular sidewall of the cartridge and the inner cross-sectional area of the dispensing outlet preferably is within the range of 30:1 to 2:1, more preferably within the range of 3:1 to 2:1 and preferably about 2.4:1. Further the inner cross-sectional area of the tubular sidewall of the cartridge is between about 30 mm² and about 40 mm², for example about 36 mm², and the inner cross-sectional area of the dispensing outlet may be between about 13 mm² and about 15 mm², for example about 14 mm².

The capacity of the dispenser is preferably between about 1 ml to about 20 ml, in more particular between about 2 ml to about 5 ml of dental material storable within the container. In a further embodiment the cartridge sidewall extends along the longitudinal axis at a substantially uniform cross-section. The sidewall further preferably has a substantially uniform thickness. The cartridge sidewall preferably extends generally circular along the longitudinal axis. The cartridge is further preferably made of a plastic material, for example polyethylene or polypropylene. The wall thickness of the cartridge sidewall is preferably between 0.6 mm and 2 mm if the cartridge is made of polypropylene. In more particular the cartridge is preferably made of a material which generally blocks light of wavelengths within the range of 380 nm to 750 nm (visible light), and more preferably in within the range of 450 nm to 495 nm (blue light). Thus the cartridge preferably protects the dental material from exposure to visible or particularly blue light during storage. Accordingly a light hardenable material which typically hardens upon exposure to light within the visible or blue light spectrum can prevented from prematurely hardening.

In a further embodiment the cover is preferably made of or comprises a material which generally blocks light of wavelengths within the range of 380 nm to 750 nm (visible light), and more preferably in within the range of 450 nm to 495 nm (blue light). The cover may particularly at least in the area in which it closes the dispensing outlet of the cartridge exhibit such light blocking property. Thus the cover at least in the area in which it closes the dispensing outlet of the cartridge preferably protects the dental material from exposure to visible or particularly blue light during storage. Accordingly a light hardenable material which typically hardens upon exposure to light within the visible or blue light spectrum can prevented from prematurely hardening.

Any light blocking effect may be provided by fillers and/or additives having opaque and/or light filtering characteristics which are merged into the material the cartridge and/or the cover are made of. Examples of such fillers comprise carbon black and orange pigments. Further any light blocking effect may be provided by a coating, for example a metal deposition coating or a varnish.

In still a further embodiment the screw plunger and/or the piston is/are made of or comprise(s) a material which generally blocks light of wavelengths within the range of 380 nm to 750 nm (visible light), and more preferably in within the range of 450 nm to 495 nm (blue light). Thus any light in the specified wavelength ranges may be blocked from entering into the cartridge from the open end of the cartridge.

In a further embodiment the cover sidewall and the cartridge sidewall in combination form a tubular double wall, wherein the cartridge sidewall is (for example generally concentrically) arranged within the cover sidewall, but with a space left between the cartridge sidewall and the cover sidewall. The cartridge sidewall is preferably dimensioned in thickness such that sufficient air permeation through the cartridge sidewall is provided. A so dimensioned cartridge sidewall may during use for dispensing dental material elastically deform due to pressure generated within the cartridge. Accordingly the cartridge, when pressurized, may elastically swell until the space between the cartridge sidewall and the cover sidewall is eliminated. At a stage in which the space between the cartridge sidewall and the cover sidewall is eliminated the cover sidewall supports the cartridge sidewall and hinders the cartridge in further swelling. In other words the swelling of the cartridge is limited by the cover. Therefore upon releasing the pressure also the shrinkage or unswelling of the cartridge to its initial dimension is limited. Any afterflow (or run-on) of the dental material after dispensation due to unswelling of the cartridge may thus be limited or minimized.

In one embodiment the cartridge sidewall outwardly may have one or more spacers for maintaining the space between the cartridge and the cover. Such a spacer may by formed by one or more bulges which are annularly distributed over the outer surface of the cartridge. Alternatively the cover sidewall inwardly may have one or more spacers for maintaining the space between the cartridge and the cover. The spacer may by formed by one or more bulges which are annularly distributed over the outer surface of the cartridge. Instead or in addition to bulges, further one or more elongated ridges may be provided on either the cartridge or the cover. Such ridges may extend linearly or helically along the longitudinal axis, for example.

In one embodiment the dispenser comprises a fill level indicator. The fill level indicator is preferably accommodated or housed within the handle. The handle preferably comprises a translucent or transparent wall portion. Further the fill level indicator is preferably arranged behind the translucent or transparent wall portion. Thus the fill level indicator is preferably visible through the translucent or transparent wall portion. The handle may further entirely or substantially entirely consist of translucent or transparent material.

In a further embodiment the handle may comprise a scale representing different fill levels. The scale is preferably arranged such that the fill indicator indicates a fill level represented on the scale. The fill level further preferably corresponds to the amount of extrudable dental material contained or remaining within the cartridge. The scale may be provided on a label which is attached on the handle. Thus during manufacturing of the dispenser the scale may be precisely adjusted to the actual amount of material filled in the cartridge. Filling tolerances may therefore provided as an add-on amount to a minimum required content of the cartridge and the label may be positioned accounting for the actual add-on amount accordingly.

In a further embodiment the translucent or transparent wall portion is colored. The color may be indicative of a particular class of a material. Thus the color of the handle may correspond to a material class encoding. The material class may concern the application for which the dental material is recommended, for example different types of a dental composite filling material for one or more of class I to V fillings, or different types of a dental composite filling material for incisal, dentin, body or enamel fillings. Further material class may concern the material type, for example the chemical composition of the dental composite filling material.

Further the dispenser may comprise a tooth color encoding indicating the tooth color which the color of the dental material contained in the dispenser approximately corresponds to. The tooth color encoding may relate to a particular material class encoding. The dispenser may comprise both, the tooth color encoding and the material class encoding. In one example the tooth color encoding corresponds to a encoding of the so-called VITA shade guide. The VITA shade guide provides certain predetermined tooth color shades indicated by a encoding, for example the encodings B1, A1, B2, D2, A2, C1, C2, D4, A3, D3, B3, A3.5, B4, C3, A4, C4, each being representative of a certain tooth color.

The cartridge preferably has a substantially ball-shaped end wall. The dispensing outlet preferably extends through that end wall at an off-center relationship to the longitudinal axis. In particular the dispensing outlet preferably extends through the end wall along a dimension which is inclined relative to the longitudinal axis. The ball-shaped cartridge end wall may have a generally uniform wall thickness and thus may exhibit an outer ball-shaped front face and an inner ball-shaped front face.

In an embodiment the dispenser comprises a piston. The piston is preferably attached to the screw plunger. The piston may be rotatably arranged on the screw plunger, in particular for a rotation about the longitudinal axis. Therefore a rotation of the screw plunger relative to the cartridge may not require the piston to also rotate. Accordingly a force required for rotating the piston relative to the cartridge may be minimized. Such force may particularly be caused by friction between the piston and the cartridge. However the piston is preferably anti-twist locked with the screw plunger. Therefore a rotation of the screw plunger about the longitudinal axis also causes the piston to rotate. It has been found that therefore at a position of the piston close to the cartridge outlet a further rotation of the piston causes the dental material to peel off from the piston and to flow out of the cartridge outlet. Thus the dispenser may be substantially entirely emptied so that the residual amount of dental material may be minimized. At least one of the cartridge, the piston and the screw plunger may be made of a material comprising a lubricant, for example a lubricant distributed within the material the cartridge/piston/plunger is/are made of. In such an embodiment the piston and the screw plunger may be anti-twist locked relative to each other or made of one piece with one another. The piston preferably has a substantially ball-shaped front face for conforming to the end wall or inner front face of the cartridge. This may further help to substantially entirely empty the dispenser from the dental material.

The threaded portion of the screw plunger in a dimension along the longitudinal axis may have a length such that the thread disengages from the nut short before or as the piston touches the cartridge at the cartridge outlet. For example the threaded portion may be recessed such that the thread of the nut is disengaged by the recess. Therefore the screw plunger may be freely rotatable in a position in which the piston touches or almost touches the cartridge at the cartridge outlet, so that dental material may be peeled off from the piston and to flow out of the cartridge outlet while the screw plunger is freely rotated.

Further the piston may in a dimension along the longitudinal axis be gas or air permeable but adapted to prevent the dental material to permeate through the piston in the same dimension. The air permeability may be provided by a passageway through the piston. The cross-sectional area of the passageway is preferably dimensioned such that air or gas can pass therethrough, whereas the dental material is hindered in passing the passageway. Therefore the piston may establish air communication between the interior of the handle and the dental material. Anaerobe polymerization of the dental material may therefore be minimized.

In a further embodiment the cover has a substantially ball-shaped end wall. The opening in the cover preferably extends through that end wall at an off-center relationship to the longitudinal axis. In particular the ball-shaped cover end wall may have a generally uniform wall thickness and thus may exhibit an outer ball-shaped front face and an inner ball-shaped front face. The inner ball-shaped front face of the cover may substantially correspond in size and shape to the outer ball-shaped front face of the cartridge. Further the opening in the cover is preferably arranged such that it can be aligned with the dispensing outlet by rotation of the cartridge and the cover about the longitudinal axis and with the outer front face of the cartridge and the inner front face of the cover in contact with each other.

In a further embodiment the cartridge is biased against the cover in a dimension along the longitudinal axis. In particular the cartridge may be biased against the cover such that the outer front face of the cartridge and the inner front face of the cover are urged in contact to each other. Thus the rotary slide valve, formed between the cartridge end wall and the cover end wall, preferably prevents dental material from flowing between the cartridge and the cover. Particularly in the storage position material stored in the cartridge may not escape from the cartridge in an area between the cartridge and the cover. It is noted that nevertheless the gap between the cartridge and the cover may exist in an area outside the end walls of the cover and the cartridge. Further the cartridge may be axially locked against movement relative to the cover along the longitudinal axis, for example by a snap lock or other appropriate connection.

In a further embodiment the cover and the handle are snap fit directly with each other. The snap fit is preferably provided by engagement of engagement structures of the handle and the cover. The snap fit further is configured to lock the handle and the cover with one another against separation in the longitudinal axis, but further to enable (preferably free) rotation of the snap locked handle and cover in the first and second direction. Further apart from the engagement structures a seal is preferably provided for sealing any gap between the cover and the handle. Accordingly the snap fit and the seal preferably are formed in separate areas. Therefore the snap fit can be configured to withstand high separation forces of the handle and the cover, whereas the seal is prevented from exposure to such high forces and thus its lifetime may be maximized.

In one embodiment the dispenser 10 has a ratchet mechanism. The ratchet mechanism may be formed by a pawl and a cam structure for cooperation with the pawl. The cam structure may be formed by a front face of the handle and the pawl may formed by a rear face of the cartridge. At an assembled stage the front face of the handle and the rear face of the cartridge preferably face each other and engage. The ratchet mechanism is preferably configured to permit a full 360 degrees rotation of the cartridge and the handle relative to each other and about the longitudinal axis A. The cam structure has preferably a plurality of first tappets and a plurality of second tappets which are arranged circumferentially about the longitudinal axis in an alternating fashion. The first and second tappets preferably each protrude from a cam base and are spaced from each other. The ratchet mechanism is preferably adapted to provide an audible click upon the pawl sliding over one of the first and second tappet and snapping back toward the cam base. The first tappet is preferably configured to permit the pawl to slide over at a rotation of the cartridge and the handle relative to each other in the first direction as well as in the second direction. However the second tappet is preferably configured to permit the pawl to slide over only at a rotation of the cartridge and the handle relative to each other in the first direction, whereas the second tappet is preferably further configured to block the pawl in a rotation of the cartridge and the handle in the second direction.

In a further embodiment the cover and the handle are spaced from each other such that a portion of the cartridge is exposed. In this embodiment the dispenser is configured such that the cartridge and the cover can be grasped by a user for opening and/or closing the dispensing outlet. Further the dispenser of this embodiment is configured such that the cartridge and the handle can be grasped by the user for dispensing the dental material. Thus the opening and/or closing function of the dispenser is separated from the dispensation function of the dispenser. In one embodiment the cover has an annular lip seal protruding from an inner surface of the cover toward an outer surface of the cartridge. The lip seal preferably surrounds the cover opening and seals with the outer surface of the cartridge. The lip seal is preferably compressed under pre-tension between the cover and the cartridge.

The dispenser of the invention preferably contains a dental material, in particular a dental composite filling material, and in more particular a light hardenable dental composite filling material. Dental composite filling materials are typically characterized by at least one or all of the following features:

a) radiation curable (especially within the region of visible light, in particular blue light);

b) formulated as a one-component composition (in contrast to e.g. dental impression materials which are formulated as two-component compositions which are mixed from a base paste and a catalyst paste shortly prior to use);

c) highly viscous;

d) slightly tacky, for example sticky if touched with the fingers;

e) "cuttable", for example can be cut into pieces with a dental instrument or knife (scalpel);

f) "firm" for example shapeable by applying manual forces but generally self-supporting in absence of such forces at least over a time period of about 5 minutes. A combination of the features (a), (b), (c) and (d) is sometimes preferred.

Dental composite materials typically comprise a hardenable resin matrix comprising hardenable components, an initiator system suitable to harden the hardenable components contained in the resin matrix and filler(s). The filler content is typically above about 50, 60 or 70 wt.-% with respect to the weight of the dental composite material. Typical ranges include from about 50 to about 90 wt.-% or from about 60 to about 80 wt.-%. The hardenable components typically comprise unsaturated moieties (carbon-carbon unsaturation) like (meth)acrylate moieties. In order to be crosslinkable, the hardenable components typically comprise at least about 2 unsaturated moieties.

The composite material may comprise only one type of filler or different types of fillers. Suitable filler(s) include fumed silica, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, barium sulphate and/or yttrium fluoride. Suitable fumed silicas include for example, products sold under the tradename Aerosil™ series OX-50, -130, -150, and -200, Aerosil R8200 available from Degussa AG, (Hanau, Germany), CAB-O-SIL™ M5 available from Cabot Corp (Tuscola, Ill.), and HDK types, e.g. HDK-H 2000, HDK H15; HDK H18, HDK H20 and HDK H30 available from Wacker. The average surface area of the silica particles is preferably greater than about 15 $m^2/g$ more preferably greater than about 30 $m^2/g$.

A "hardenable component or material" or "polymerizable component" is any component which can be cured or solidified e.g. by radiation-induced polymerization. A hardenable component may contain only one, two, three or more polymerizable groups. Typical examples of polymerizable groups include unsaturated carbon groups, such as a vinyl group being present i.a. in a (methyl)acrylate group.

"(Meth)acryl" is a shorthand term referring to "acryl" and/or "methacryl". For example, a "(meth) acryloxy" group is a shorthand term referring to either an acryloxy group (i.e., CH2=CH—C(O)—O—) and/or a methacryloxy group (i.e., CH2=C(CH3)-C(O)—O—).

A "curing, hardening or setting reaction" is used interchangeable and refers to a reaction wherein physical properties such as viscosity and hardness of a composition changes over the time due to a chemical reaction between the individual components.

"Light hardenable" shall mean that the composition can be cured by applying radiation with light, preferably radiation with light at a wavelength within the visible light spectrum under ambient conditions (for example approximately 23±10 degrees Celsius) and within a reasonable time frame (e.g. within about 15, 10 or 5 minutes).

The term "visible light" is used to refer to light having a wavelength of about 380 to about 750 nanometers (nm).

The invention further relates to a method of dispensing a dental composite filling material. The method comprises the steps of:

providing a dispenser of the invention, the dispenser having a handle and a cover which are rotatable relative to each other about a longitudinal axis of the dispenser;

rotating the handle and the cover in a first direction about the longitudinal axis and thereby extruding a portion of the dental composite filling material;

rotating the handle and the cover in a second direction opposite of the first direction about the longitudinal axis and thereby cutting off the portion of the dental composite filling material; and removing the cut off portion of the dental composite filling material.

The method may further comprise the step of rotating the handle and the cover in the first direction about the longitudinal axis and thereby positioning the dispenser from the storage position to the dispensing position. The step of removing the cut off portion of the dental composite filling material may be performed without or substantially without a cutting or scraping action by a dental instrument. Thus the risk of contaminating the dental material with a cut off particle of the dispenser may be minimized. Further due to cutting of the dental material by operating the dispenser toward the storage position the dispenser is normally closed when the dental material is picked up for use. Accordingly an instrument used for picking up dental material is prevented from getting into contact with dental material still stored in the dispenser. Therefore the risk of cross-contamination between two patients treated by use of the same dispenser is minimized. Further because a contact between the instrument and the dispenser is not necessary contamination of the dispenser as such may also be avoided. Therefore the invention helps maximizing the hygiene in a dental treatment using the dispenser.

DETAILED DESCRIPTION OF THE INVENTION

Figure 1:
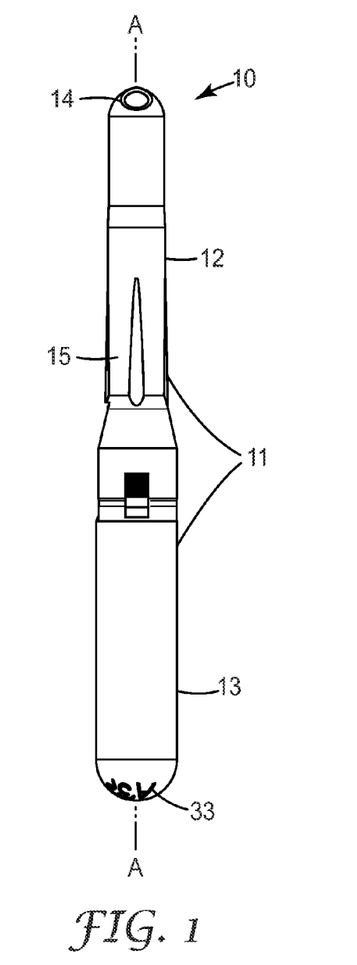
FIG. 1 is a side view of a dispenser according to an embodiment of the invention.

FIG. 1 shows a dispenser 10 according to the invention. The dispenser has a housing 11 which is formed of a cover 12 and a handle 13. The dispenser 10 extends generally straight along a longitudinal axis A. The longitudinal axis A in the example also forms an axis of symmetry of the dispenser 10. For dispensation of the dental material the cover 12 has an opening 14 (sometimes referred to as "cover opening" herein). In the example shown the opening 14 is closed. The handle 13 and the cover 12 are rotatably interconnected with each other such that the handle 13 and the cover 12 can be rotated relative to each other about the longitudinal axis A. Thus dental material can be dispensed from the dispenser by rotating the handle 13 and the cover 12 against each other. In particular, the dispenser is adapted such that the opening 14 can be opened by rotating the handle 13 and the cover 12 relative to each other in a first direction, and such that a further rotation in the same direction causes the dental material to be dispensed. The dispenser is further adapted such that a rotation of the handle 13 and the cover 12 in a second direction opposite of the first direction causes the opening 14 to close and thereby to shear off a portion of dental material extending through the opening 14.

The plane of the interconnection between the handle 13 and the cover 12 is preferably offset along the longitudinal axis A from to the center of the dispenser. In particular the interconnection between the handle 13 and the cover 12 is preferably offset from the center toward the handle 13. In other words the handle 13 is preferably smaller in length than the cover 12. In this regard the "length" of the dispenser refers to the size of the dispenser in a dimension parallel to the longitudinal axis. Thereby the dispenser is adapted such that it can be held at the cover 12 for example by three fingers and operated by rotating the handle 13 by the thumb and the forefinger. This has been found to provide a relative convenient operability of the dispenser.

Figure 1A:
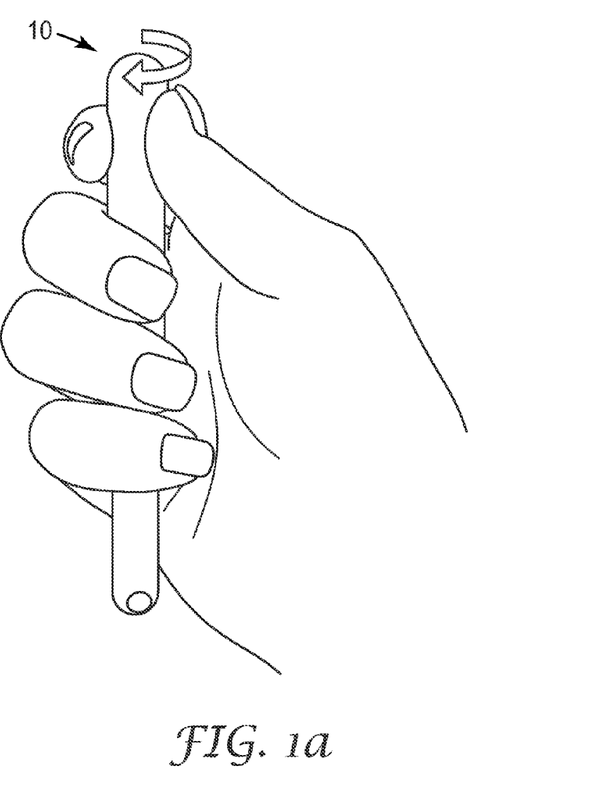
FIG. 1a is a view of the dispenser shown in FIG. 1 held in a hand.

The dispenser 10 accordingly is shaped such that it can be held in a user's hand as illustrated in FIG. 1a. The largest diameter of the dispenser 10 may be within a range of 10 mm to 15 mm. Thus the dispenser 10 may be conveniently held by hand and may allow for convenient operation of the dispenser 10. The dispenser 10 further may have an outward gripping structures, like one or more grooves or ribs extending along a dimension parallel to the longitudinal axis A, or pimples distributed over the outside of the handle 13 and/or the cover 12. In the example the cover has outward gripping structures in the form of ribs 15 which extend along a dimension parallel to the longitudinal axis A and which are uniformly distributed over the circumference of the cover 12. Although not shown, similar or other appropriate gripping structures may be provided at the handle 13.

The handle 13 further exhibits a tooth color encoding 33 which in the example is arranged on an outer surface of a ball-shaped end of the handle 13. The ball-shape enables the tooth color encoding 33 to be recognized when viewed from an axial viewing perspective (for example when the dispenser is stored in a stand with the handle 13 oriented upwards) relative to the longitudinal axis A as well as from a radial viewing perspective (for example when the dispenser is stored in a drawer).

Figure 2:
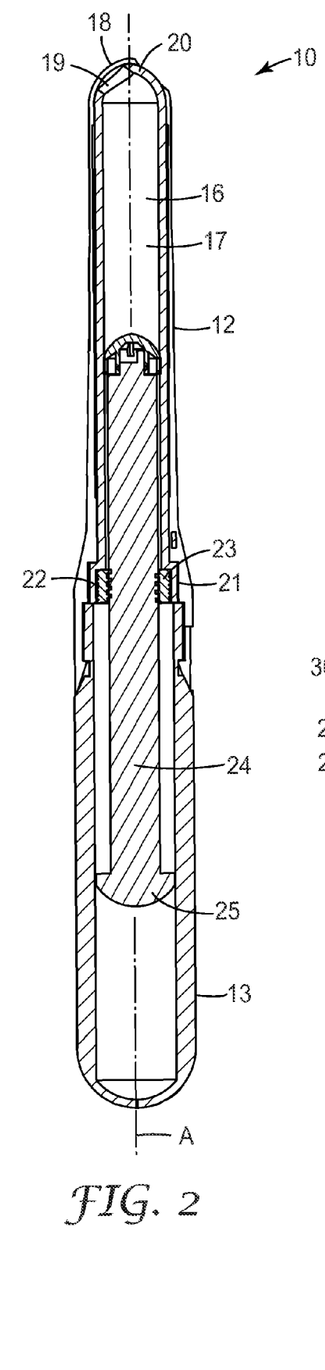
FIG. 2 is a cross-sectional view of the dispenser according to an embodiment of the invention.

FIG. 2 shows the dispenser 10 in a cross-sectional view in more detail. The dispenser 10 has a cartridge 16 for storing the dental material (not shown). The cartridge 16 extends along the longitudinal axis A at a generally circular inner and outer cross-section. Thus the cartridge has a tubular section with a generally cylindrical outer shape and a generally cylindrical inner shape. The cartridge 16 further forms a chamber 17 for containing the dental material. The cartridge 16 has a dispensing outlet 19 for the dental material. The dispensing outlet 19 is formed through an end wall 20 of the cartridge 16. The end wall 20 is substantially ball-shaped inwardly and outwardly, and thus has a generally uniform wall thickness. Further the dispensing outlet 19 is arranged through the end wall 20 of the cartridge 16 at an off-center relationship to the longitudinal axis A. The cartridge 16 is received within the cover 12.

The cover 12 also extends along the longitudinal axis A at least at a generally circular inner cross-section, and may have an essentially circular outer cross-section. Therefore the cover 12 has a tubular section with at least a generally cylindrical inner shape. Although the tubular section of cover 12 may have gripping structures as shown in FIG. 1 it still may in essence—except at the area of the gripping structures—have a cylindrical outer shape. The cover 12 further has an end wall 18 which is at least inwardly substantially ball-shaped. Further the inner side of the end wall 18 is shaped to generally match with the outside of the end wall 20 of the cartridge 16. Preferably the end wall 18 is inwardly and outwardly substantially ball-shaped and thus has preferably a generally uniform wall thickness. Further the opening 14 is arranged through the end wall 18 of the cover 12, preferably at an off-center relationship to the longitudinal axis A. In particular the dispensing outlet 19 and the cover opening 14 are arranged such that they can be aligned with each other in a situation in which the cartridge 16 and the cover 12 are mated with each other. In this regard the term "mated" refers to the cartridge 16 being received within the cover 12 such that the outer side of the end wall 20 of the cartridge 16 is in contact with the inner side of the end wall 18 of the cover 12.

The inner diameter of the tubular section of the cover 12 is greater than the outer diameter of the tubular section of the cartridge 16. Thus a gap is provided between the tubular sections of the cartridge 16 and the cover 12. On the other hand the cover 12 and the cartridge 16, in particular the tubular sections of the cover 12 and the cartridge 16, are sized such that the gap has a predetermined maximum size. The maximum size of the gap is preferably predetermined such that an expansion or swelling of the cartridge 16—caused by a pressure exerted to the dental material contained in the cartridge for dispensation—is restricted by the cover 12. In other words the cover 12 and the cartridge 16 are sized such that the cover 12 supports the cartridge 16 against expansion during dispensation of dental material, but also such that during storage the gap exists. Further such a double wall construction, provided by the wall of the cover 12 and the wall of the cartridge 16, allows for minimizing the thickness of the cartridge wall, because the cover 12 can mechanically back up or support the pressurized cartridge and avoid rupturing of the pressurized cartridge. As a result the invention enables appropriate air permeation from the gap through the cartridge wall during storage of the dental material. Air permeation through the cartridge walls helps avoiding undesirable anaerobic polymerization of certain dental materials, like for example dental composite filling materials. The invention further enables the dental material to be dispensed at relatively high pressures. Such high pressures may be required particularly for dispensing high viscosity dental composite filling materials. It has been found that due to limiting the ability for expansion further any retraction of the cartridge after releasing the pressure from the cartridge is limited. Afterflow or run-on, typically caused by elastic retraction of the cartridge and causing further dental material to be extruded unintentionally, may thus be avoided. Because the cartridge 16 is further axially locked against movement relative to the cover 12 along the longitudinal axis, an expansion in a dimension of the longitudinal axis during dispensation of dental material may also be limited, and consequently run-on caused by retraction in the same dimension may be limited.

Figure 3:
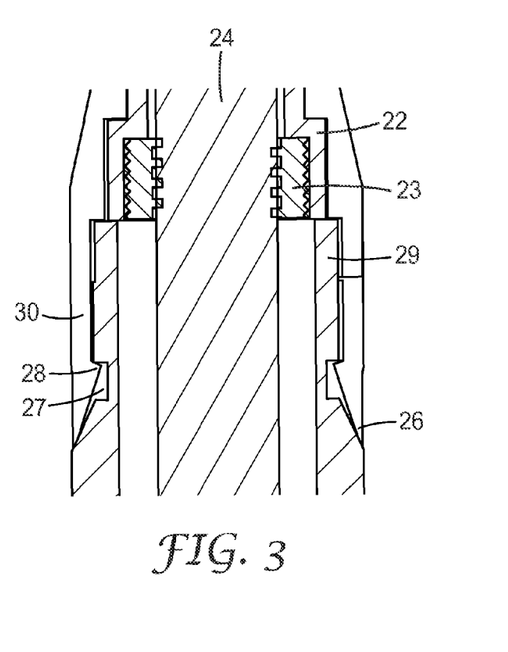
FIG. 3 is an enlarged partial view of FIG. 2.

The cartridge 16 at a rear end 21 has a flange 22 which accommodates a threaded nut 23 in engagement with a threaded screw plunger 24. An enlarged illustration of the cartridge flange 22, the threaded nut 23 and a portion of the screw plunger 24 are shown in FIG. 3. In the example the threaded nut 23 has an inner thread for engagement with an outer thread of the screw plunger 24. The threaded nut 23 further has an outer thread for engagement with an inner thread of the cartridge flange 22. The skilled person will recognize that the threaded nut 23 may be otherwise retained with the cartridge. For example the threaded nut 23 may be snap fit, press fit, welded or glued within the flange 22 of the cartridge. It may further be possible to form the nut 23 in one piece (for example monolithically) with the cartridge 16. The dispenser 10 is thus adapted such that the screw plunger 24 can be screwed into cartridge 16 for advancing the dental material toward the dispensing outlet 19. The pitch of the outer thread of the screw plunger 24 and the inner thread of the nut 23 may be minimized to maximize the force for dispensing the dental material. In a preferred embodiment the pitch of the thread is in a range of 0.5 mm and 2 mm, preferably about 1 mm. In another example (not shown) the nut may be formed of two or more annular segments which allow the nut to be assembled on the screw plunger by lateral placement (rather than by screwing action) onto the screw plunger. For example the nut may be formed of two annular half sections which are hinged with each other at one side and which, for forming the closed nut, have retention elements for interlocking the half sections with each other at the other side.

The dispensing outlet 19 can be closed by the cover 12 as shown in the example. Relative to the situation shown, the cartridge 16 and the cover 12 may further be rotated about the longitudinal axis A such that the dispensing outlet 19 is aligned with the opening 14 (cover opening 14 visible in FIG. 1). Accordingly the cartridge 16 and the cover 12 in combination form a rotary slide valve which is operable between a storage position, in which the cover 12 closes the dispensing outlet 19 of the cartridge, and a dispensing position, in which the opening 19 in the cover 12 opens the dispensing outlet 19 of the cartridge.

The screw plunger 24 is received within the handle 13. In particular the screw plunger 24 within the handle 13 is arranged axially displaceable but locked against rotation relative to the handle 13. Accordingly a relative rotation between the screw plunger 24 and the handle 13 about the longitudinal axis A is restricted. In the example an anti-rotation lock is provided by a non-circular head 25 of the screw plunger 24 which engages a correspondingly shaped inner profile of the handle 13. Although not shown, the skilled person will recognize other anti-rotation mechanisms, like for example a groove within the screw plunger engaging with a detent in the handle, or one or more longitudinal flats within the screw plunger and a corresponding profile in the handle.

Further the cartridge 16 within the cover 12 is rotatable relative to the cover 12 within predetermined limits only and blocked against a rotation beyond such limits. The dispenser 10 is thus adapted such that a relative rotation between the cartridge 16 and the cover 12 about the longitudinal axis A is enabled within a predetermined rotation angle and restricted otherwise. Accordingly the dispenser is adapted such that a rotation of the handle 13 and the cover 12 relative to each other can also cause the screw plunger 24 and the cartridge 16 to rotate relative to each other. Thereby the cartridge 16 and the screw plunger 24 may not rotate relative to each other within the predetermined limits within which the cartridge 16 and the cover 12 can rotate relative to each other, but rotate relative to each other upon a rotational position has been reached in which the rotation between the cartridge 16 and the cover 12 is blocked. This provides for the dispenser to automatically open upon rotating the cover 12 and the handle 13 relative to each other in the first direction, and for the dispenser to dispense dental material upon further rotating the cover 12 and the handle 13 of the so opened dispenser 10 in the first direction. Further a rotating of the cover 12 and the handle 13 relative to each other in the second direction causes the dispenser to automatically close.

The dispenser 10 may have a ratchet mechanism which suspends the engagement between the screw plunger 24 and the handle 13 during a rotation of the cover 12 and the handle 13 in the second direction relative to each other. The dispenser 10 may further have a ratchet mechanism which blocks or restricts a rotation between the cartridge 16 and the screw plunger 24 during a rotation of the cover 12 and the handle 13 in the second direction relative to each other. Thus a retraction of the screw plunger 24 and the entering of air into the cartridge 16 are avoided. The ratchet mechanisms may be combined or replaced by a ratchet mechanism providing for both, suspending engagement and blocking rotation as described.

Further the dispenser 10 is preferably adapted to provide an audible click per each predetermined rotation angle which the cover 12 and the handle 13 are rotated relative to each other. Thus the amount of dental material dispensed can be easily metered by a user of the dispenser 10 paying attention for the clicks. Preferably the ratchet mechanism is adapted such that it permits a rotation between the cartridge 16 and the screw plunger 24 in the second direction relative to each other for a (preferably short) predetermined angular movement. Thus during a rotation of the handle 13 and the cover 12 toward the storage position the screw plunger 24 preferably over a limited angle rotate relative to each other in the second direction and thereby retract the screw plunger 24 (and the piston) over a short distance. Such a slight retraction preferably causes any remaining pressure on the dental material to relieve and thus to avoid afterflow or run-on of the dental material. A so adapted ratchet mechanism may comprise a toothing having teeth with an undercut and a pawl which can move into the undercut only once it has engaged a tooth. Accordingly if the cartridge 16 and the screw plunger 24 are rotated in the first direction relative to each other the pawl may engage a tooth and once it has engaged the tooth the pawl may be movable toward the undercut upon rotation of the cartridge 16 and the screw plunger 24 in the second direction relative to each other.

The dispenser 10 further has a seal 26 which is arranged between the handle 13 and the cover 12. In particular the handle 13 and the cover 12 are adapted for mating with each other by means an overlap fitting, and the seal 26 is arranged to seal a gap between overlapping portions of the cover 12 and the handle 13. In the example the handle 13 has a first fitting member 29 forming the male part of the fitting and the cover 12 has a second fitting member 30 forming the female part of the fitting. The first and second fitting members 29, 30 are adapted for mating with each other such that they overlap with each other when mated. The cover 12 and the handle 13 are further snap fit preferably directly with each other. The snap fit is provided by engagement of engagement structures provided at the handle 13 and the cover 12. In the example a recess 27 is provided as a first engagement structure in the first fitting member 29, and a retainer 28 is provided as a second engagement structure in the second fitting member 30. The recess 27 and the retainer 28 are adapted for engaging with one another. Thus once the handle 13 and the cover 12 are snap fit with each other so that also the recess 27 and the retainer 28 engage with each other, the handle 13 and the cover 12 are locked against separation from each other along a dimension parallel to the longitudinal axis A. Further in the example the recess 27 is preferably formed as a circumferential groove and the retainer 28 is preferably formed as a circumferential bulge. Accordingly once the handle 13 and the cover 12 are snap fit with each other so that also the recess 27 and the retainer 28 engage with each other, the handle 13 and the cover 12 are enabled for a rotation relative to each other about the longitudinal axis A. The seal 26 is preferably provided apart from the engagement structures. In particular the seal 26 in the example is provided spaced from the engagement structures. Further the engagement structures are located outside the interior sealed by the seal 26.

Figure 4:
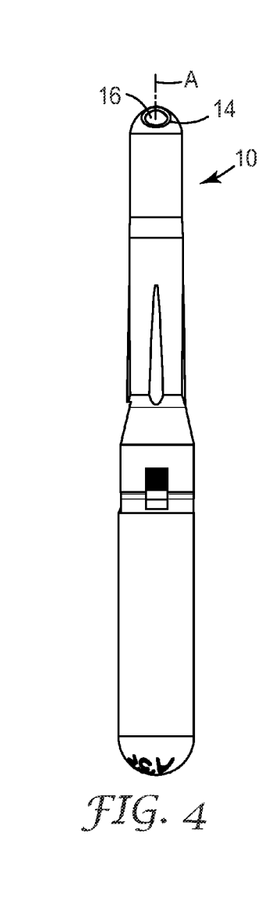
FIGS. 4-8 illustrate an operation of the dispenser according to an embodiment of the invention.
Figure 5:
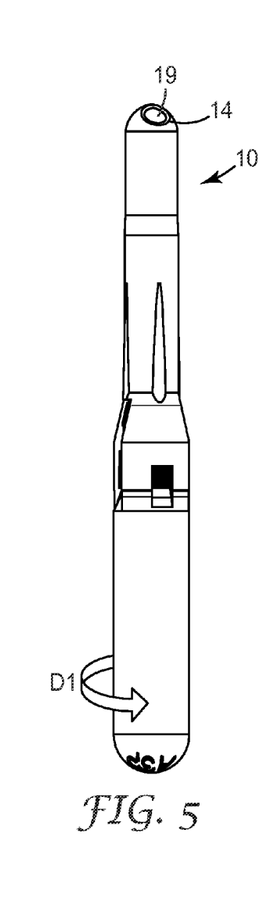
Figure 6:
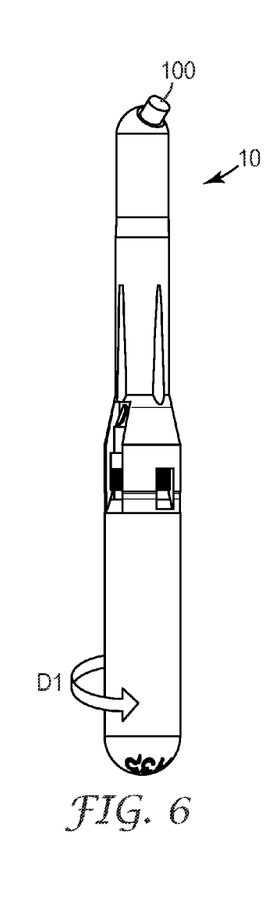
Figure 7:
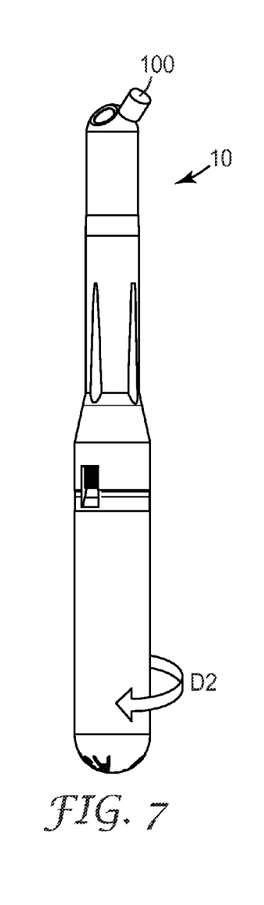
Figure 8:
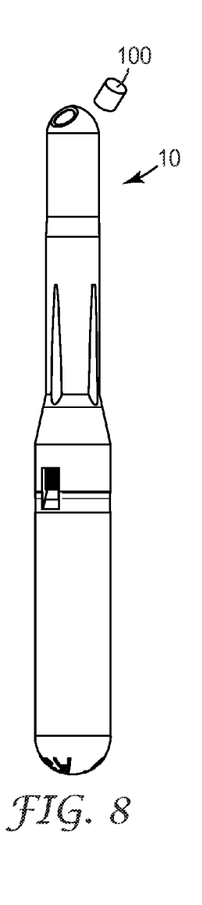

FIGS. 4 to 8 illustrate the operation of the dispenser 10. FIG. 4 shows the dispenser 10 in the storage position, in which the dispensing outlet 19 (reference number indicated in FIG. 5) of the cartridge 16 is closed by the cover 12. A portion of the cartridge 16 is exposed within the opening 14 of the cover 12. FIG. 5 shows the dispenser in the dispensing position. The dispensing position is reached by rotating the handle 13 and the cover 12 in the first direction D1 about the longitudinal axis A relative to each other. (The arrow indicates the first direction D1 for the example that the handle 13 is rotated relative to the cover 12 without rotating the cover 12) The rotation angle for bringing the dispenser 10 from the storage position to the dispensing position is preferably equal or less than 180 degrees, in particular about 90 degrees. In the dispensing position the dispensing outlet 19 and the cover opening 14 are aligned with each other. FIG. 6 shows the dispenser 10 in the use position, in which some dental material 100 is extruded from the cartridge 16, which therefore protrudes from the dispensing outlet 19. In the use position the dispensing outlet 19 and the cover opening 14 are also aligned with each other. Relative to the dispensing position the use position can be reached by, starting from the dispensing position, further rotating the handle 13 and the cover 12 in the first direction D1 about the longitudinal axis A relative to each other. The amount of dental material extruded from the cartridge 16 is proportional to the rotation angle by which the handle 13 and the cover 12 are rotated relative to each other. The dispenser 10 may be adapted such that each rotation about a predetermined rotation angle provides an audible and optionally tactile click to a user of the dispenser 10. For example the dispenser 10 may be adapted such that the handle 13 and the cover 12 audibly and/or tangibly rest in predetermined rotational positions relative to each other during rotation. FIG. 7 shows the dispenser 10 back in the storage position and thus corresponds to the stage as shown in FIG. 4. However the dental material 100 is placed on the dispenser in the storage position shown in FIG. 7. From the use position the storage position can be reached by rotating the handle 13 and the cover 12 in the second direction D2 (opposite to the first direction D1) about the longitudinal axis A relative to each other. Thereby the cover 12 and the cartridge 16 rotate relative to each other and also the cover opening 14 and the dispensing outlet 19 displace relative to each other, in particular the cover opening 14 and the dispensing outlet 19 move apart from each other. Accordingly a portion of the dental material extending through the opening 14 and the outlet 19 is sheared off by the end walls 20, 18 of the cartridge 16 and the cover 12, respectively. The dental material 100 in the example slightly adheres to cover 12 and/or the cartridge 16 (exposed through the opening 14 of the cover 12). Accordingly the sheared-off portion of dental material 100 is made available ready to be taken away by a user as indicated in FIG. 8. The sheared-off portion of dental material may be taken away by any appropriate dental instrument, like for example a Heidemann spatula. Therefore scraping or cutting off the dental material, for example from a bulk or strand of dental material, can be avoided. Further the risk of scraping off particles from the dispenser can be minimized, because the already sheared-off portion of dental material may be picked up by an instrument without or with only soft contact between the dispenser and the instrument.

Figure 9:
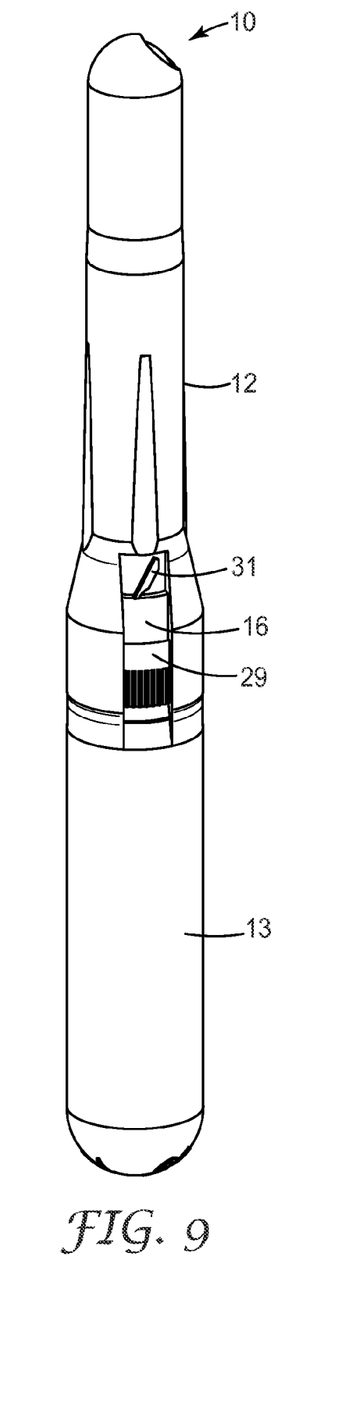
FIG. 9 is a side view including a virtual cutaway of the dispenser according to an embodiment of the invention.

FIG. 9 shows the dispenser 10 with a virtual cut-away in cover 12 to provide a view on a spring 31 which is arranged at the cartridge 16. Further a circumferential toothing 32 is partially shown on the first fitting member 29 of the handle 13. The virtual cut-away including the spring 31 and the toothing 32 is shown enlarged in FIG. 10. The spring 32 is arranged such that the cover 12 and the cartridge 16 are urged toward the storage position. This means that in the storage position as shown the spring 31 is unloaded or under a predetermined first pretension. The cover 12 and the cartridge 16 can only be rotated toward the dispensing position against a force of the spring 31 so that in the dispensing position the spring is put under load (toward a second higher pretension) and urges the cover 12 and the cartridge 16 back toward the storage position. In the example the spring 31 is a leaf spring which is arranged for engagement with a projection at the inside the cover 12. The skilled person will however recognize other mechanisms for resiliently urging the cover 12 and the cartridge 16 toward the storage position. In particular the spring may likewise be part of the cover 12 or a separate part, and a projection or other means may be present at the cartridge 16 and/or the cover 12.

Figure 10:
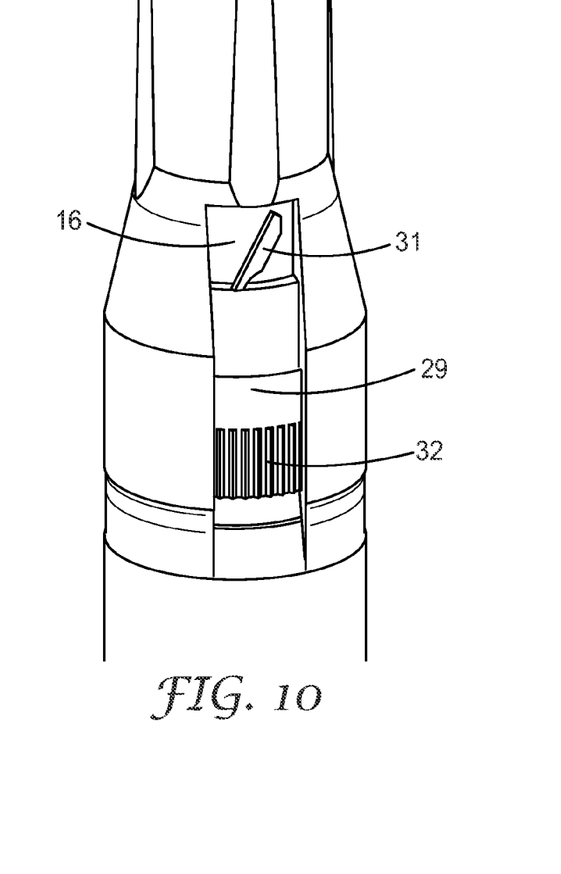
FIG. 10 is an enlarged partial view of FIG. 9.

The toothing 32 at the handle 13 preferably engages with a preferably flexible pawl (not shown in detail) at the inside of cover 12. The toothing 32 in the example has a uniform pitch over the circumference. Accordingly the pawl and the toothing 32 repeatedly engage and disengage with each other as the handle 13 and the cover 12 are rotated relative to each other. In this regard the term "engage" refers to the pawl to engage between two teeth of the toothing, whereas the term "disengage" refers to the pawl to slide over a head of a tooth. Thereby the toothing and the pawl preferably cause an audible and tactile click for a user rotation the handle 13 and the cover 12.

Figure 11:
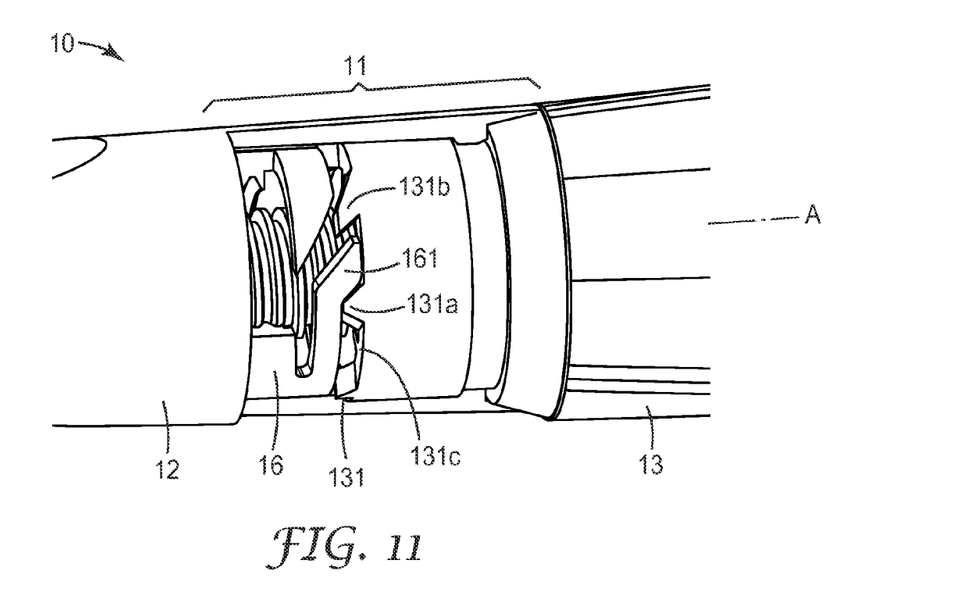
FIG. 11 is a partial exploded view of the dispenser according to an embodiment of the invention.

FIG. 11 shows a portion of the dispenser 10 in an exploded assembly view. The dispenser 10 has a housing 11 which is formed of a cover 12 and a handle 13. A cartridge 16 for storing the dental material is received within the housing 11. The configuration of the dispenser 10 and the components the dispenser consists of are identical to the embodiment described in FIGS. 1-3, except for the dispenser 10 in the example of FIG. 11 having a ratchet mechanism formed by a pawl 161 and a cam structure 131 for cooperation with the pawl 161. In particular the cam structure 131 is formed by a front face of the handle 13 and the pawl 161 is formed by a rear face of the cartridge 16. At an assembled stage the front face of the handle 13 and the rear face of the cartridge 16 face each other and are arranged for cooperation with each other. The ratchet mechanism is configured to permit a full 360 degrees rotation of the cartridge 16 and the handle 13 relative to each other and about the longitudinal axis A. The cam structure 131 has a plurality of first tappets 131a and a plurality of second tappets 131b which are arranged circumferentially in an alternating fashion. The first and second tappets 131a, 131b protrude from a cam base 131 c and are spaced from each other. Rotating the cartridge 16 and the handle 13 relative to each other in the first direction therefore causes the pawl 161 to slide over one of the first and second tappets 131a, 131b, to snap back toward the cam base 131c, to slide over the other one of the first and second tappets 131a, 131b, snap back toward the cam base 131c, and so on. Each time the pawl 161 snaps back toward the cam base 131c the ratchet mechanism provides an audible click. Such click indicates a user that the cartridge 16 and the handle 13 handle have been rotated by a certain predetermined angle and thus indicates the dispensation of a predetermined amount of dental material from the dispenser 10. The first tappet 131a is configured to permit the pawl 161 to slide over at a rotation of the cartridge 16 and the handle 13 in the first and the second direction. However the second tappet 131 is configured to permit the pawl 161 to slide over only at a rotation of the cartridge 16 and the handle 13 in the first direction, whereas the second tappet 131 is configured to block the pawl 161 in a rotation of the cartridge 16 and the handle 13 in the second direction. The first tappet 131a has two opposite flanks forming a obtuse angle with the cam base 131c, whereas the second tappet 131b has one flank forming a obtuse angle with the cam base 131c and an opposite further flank forming a acute angle with the cam base 131c. The flank forming the acute angle with the cam base 131c provides for blocking the pawl 161 from sliding over the second tappet 131b, whereas any flanks forming a obtuse angle with the cam base 131c permit sliding over the respective tappet 131a/131b. Thus the ratchet mechanism permits a rotation of the cartridge 16 and the handle 13 in the second direction only within a limited predetermined first angle which is smaller than 360 degrees, for example 180 degrees, 120 degrees, 90 degrees, or any other angle as appropriate. Accordingly the ratchet mechanism is adapted to limit a rotation in the second direction within the first angle, whereas the ratchet mechanism is additionally adapted to audibly indicate a rotation about a smaller second angle.

Therefore the dispenser 10 allows for relatively precisely dispensing even small amounts of dental material and additionally provides for a reverse rotation lock. The obtuse angle of the flank of the second tappet 131b preferably is greater than the obtuse angle of the corresponding flank (the flank oriented in the same rotational direction) of the first tappet 131a. Thus sliding of the pawl 161 over the second tappet 131b requires less torque to rotate the handle 13 and the cartridge relative to each other in the first direction than sliding of the pawl 161 over the first tappet 131a. Therefore the user can sense the rotational position of the handle 13 and the cartridge 16. Preferably the pawl 161 is monolithically formed (for example injection molded) with the remainder of the cartridge 16. Thus efforts and cots for assembly of the dispenser may be minimized.

Figure 12:
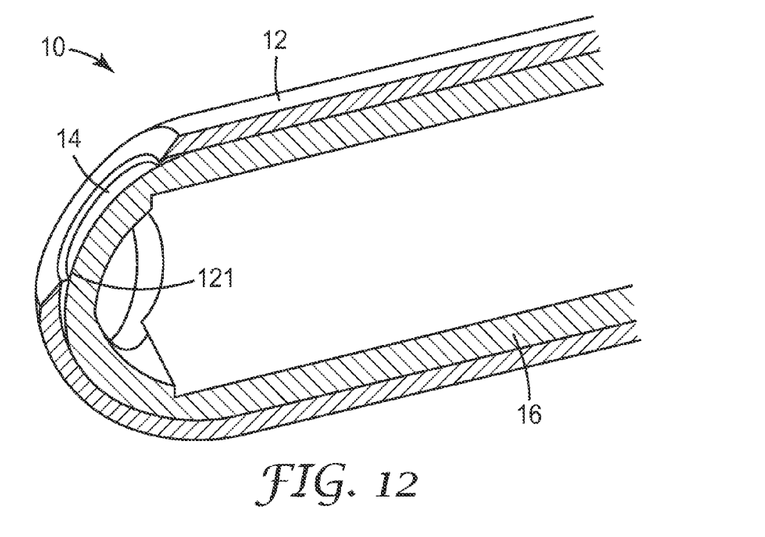
FIG. 12 is a partial cross-sectional view of the dispenser according to an embodiment of the invention.

FIG. 12 shows a dispenser 10 in which the cover 12 has an annular lip seal 121 which protrudes from an inner surface of the cover 12 toward the cartridge 16. The lip seal 121 surrounds the cover opening 14 and seals with an outer surface of the cartridge 16. Accordingly the lip seal is preferably compressed under pre-tension between the cover 12 and the cartridge 16. In particular in the dispensing position the lip seal 121 further surrounds the dispensing outlet (not visible in this view) of the cartridge 16. The lip seal 121 preferably tapers toward its free end and further the cross-sectional profile of the lip seal 121 tapers toward the free end. Therefore material dispensed from the cartridge is prevented from flowing between the cover 12 and the cartridge 16. Further the lip seal 121 provides for precise cutting off of the material protruding over the dispensing outlet.

Figure 13:
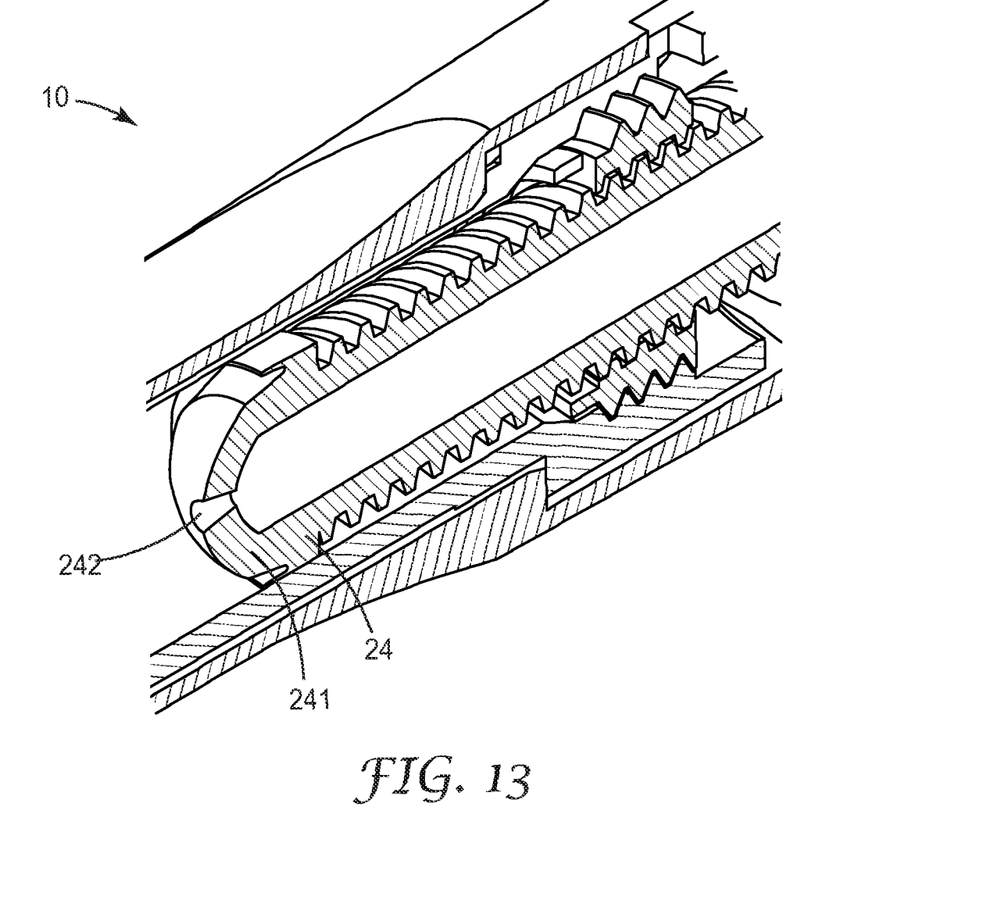
FIG. 13 is a partial cross-sectional view of the dispenser according to a further embodiment of the invention.

FIG. 13 shows a dispenser 10 having a screw plunger 24 which forms a piston 241 in one monolithic piece with the plunger 24. The piston 241 at a dental material facing side has a through-hole 242 which is small enough to prevent dental material to pass therethrough but which is adapted to permit air to pass through. The though-hole 241 is preferably in fluid communication with the hollow inside of the handle and thus with a larger reserve of air. This allows exposing the dental material with a sufficient amount of air to avoid anaerobic polymerization during storage over a longer time period.

The invention claimed is:

1. A pen-like dispenser for dispensing a dental material, comprising:
    a handle and a cover which are rotatable relative to each other about a longitudinal axis of the dispenser, the cover having an opening, and wherein the cover and the handle are snap fit directly with each other, and wherein the snap fit is provided by engagement of engagement structures of the handle and the cover;
    a seal for sealing any gap between the cover and the handle;
    a cartridge for holding the dental material and having a dispensing outlet for the dental material; and
    a screw plunger for extruding the dental material from the cartridge by screwing action,
    the cartridge and the cover in combination forming a rotary slide valve which is operable by rotation about the longitudinal axis between a storage position, in which the cover closes the dispensing outlet of the cartridge, and a dispensing position, in which the opening in the cover opens the dispensing outlet of the cartridge,
    wherein a relative rotation between the screw plunger and the handle about the longitudinal axis is restricted in both forward and backward directions, and wherein a relative rotation between the cartridge and the cover about the longitudinal axis is enabled within a predetermined rotation angle and restricted otherwise.

2. The dispenser of claim 1, wherein, for at least over a part of a length of the handle, the handle has a uniform non-circular inner cross-section, and wherein the screw plunger comprises an outer cross-section which is shaped to engage with the inner cross-section of the handle so that a relative rotation between the screw plunger and the handle is restricted but movement along the longitudinal axis is enabled.

3. The dispenser of claim 1, further comprising a return spring for resiliently biasing the cover toward the storage position to return the cover automatically from the dispensing position to the storage position by spring force.

4. The dispenser of claim 3, wherein the return spring is configured such that it provides a force sufficient to return the cover to the storage position and thereby to cut off dental material extending through the open rotary slide valve by spring force.

5. The dispenser of claim 1, wherein a gap is provided between the cartridge and the cover over at least a portion of the cartridge circumference about the longitudinal axis.

6. The dispenser of claim 1, the handle comprising a translucent or transparent wall portion.

7. The dispenser of claim 6, wherein the translucent or transparent wall portion has a color indicative of a particular class of a material.

8. The dispenser of claim 1, further comprising a tooth color encoding indicating the tooth color which the color of the dental material contained in the dispenser approximately corresponds to.

9. The dispenser of claim 1, wherein the cartridge has a ball-shaped end wall through which the dispensing outlet extends at an off-center relationship to the longitudinal axis.

10. The dispenser of claim 9, further comprising a piston which is rotatably arranged on the screw plunger.

11. The dispenser of claim 10, wherein the piston has a ball-shaped front face for conforming to the end wall of the cartridge.

12. The dispenser of claim 10, wherein the piston in a dimension along the longitudinal axis is gas or air permeable and prevents the dental material to permeate through the piston in the same dimension.

13. The dispenser of claim 1, wherein the cartridge has a sidewall extending along the longitudinal axis at a uniform cross-section, and wherein the sidewall has a uniform thickness.

14. A method of dispensing a dental composite filling material, comprising:
providing a dispenser of claim 1;
rotating the handle and the cover in a first direction about the longitudinal axis and thereby extruding a portion of the dental composite filling material;
rotating the handle and the cover in a second direction opposite of the first direction about the longitudinal axis and thereby cutting off the portion of the dental composite filling material; and
removing the cut off portion of the dental composite filling material.

* * * * *

UNITED STATES PATENT AND TRADEMARK OFFICE
CERTIFICATE OF CORRECTION

PATENT NO.       : 10,016,257 B2
APPLICATION NO.  : 14/785029
DATED            : July 10, 2018
INVENTOR(S)      : Helmut Pauser et al.

Page 1 of 1

It is certified that error appears in the above-identified patent and that said Letters Patent is hereby corrected as shown below:

In the Specification

Column 6
Line 16, Delete "may by" and insert -- may be --, therefor.

Column 6
Line 21, Delete "may by" and insert -- may be --, therefor.

Column 10
Line 13 (approx.), Delete "CH2=CH" and insert -- CH2=CH --, therefor.

Column 10
Line 14 (approx.), Delete "CH2=C" and insert -- CH2=C --, therefor.

In the Claims

Column 19
Line 28, In Claim 8, delete "claim 1," and insert -- claim 1 --, therefor.

Signed and Sealed this
Sixteenth Day of April, 2019

Andrei Iancu
*Director of the United States Patent and Trademark Office*